US012296032B2

(12) United States Patent
Hoffmann et al.

(10) Patent No.: US 12,296,032 B2
(45) Date of Patent: May 13, 2025

(54) PROCESS OF TAKING A DENTAL IMPRESSION WITH A RADIATION-CURABLE COMPOSITION CONTAINING MERCAPTO-FUNCTIONAL POLYORGANOSILOXANES AND VQM RESINS

(71) Applicant: Solventum Intellectual Properties Company, Maplewood, MN (US)

(72) Inventors: Henning Hoffmann, Windach (DE); Peter U. Osswald, Tuerkheim (DE); Peter Bissinger, Diessen (DE); Joachim W. Zech, Kaufering (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 649 days.

(21) Appl. No.: 17/595,997

(22) PCT Filed: Jun. 9, 2020

(86) PCT No.: PCT/IB2020/055409
§ 371 (c)(1),
(2) Date: Dec. 1, 2021

(87) PCT Pub. No.: WO2020/250129
PCT Pub. Date: Dec. 17, 2020

(65) Prior Publication Data
US 2022/0226201 A1    Jul. 21, 2022

(30) Foreign Application Priority Data
Jun. 12, 2019  (EP) ..................... 19179611

(51) Int. Cl.
A61K 6/90      (2020.01)
A61C 9/00      (2006.01)

(52) U.S. Cl.
CPC .............. *A61K 6/90* (2020.01); *A61C 9/0006* (2013.01)

(58) Field of Classification Search
CPC ...................................................... A61K 6/90
See application file for complete search history.

(56) References Cited

U.S. PATENT DOCUMENTS

| | | |
|---|---|---|
| 1,509,376 A | 9/1924 | Rodgers |
| 3,242,218 A | 3/1966 | Miller |
| 4,035,453 A | 7/1977 | Hittmair |
| 4,657,959 A | 4/1987 | Bryan |
| 4,737,593 A | 4/1988 | Elrich |
| 4,782,101 A | 11/1988 | Waller |
| 5,100,929 A | 3/1992 | Jochum |
| 5,487,662 A | 1/1996 | Kipke |
| 5,750,589 A | 5/1998 | Zech |
| 5,878,907 A | 3/1999 | Graf |
| 6,046,250 A | 4/2000 | Boardman |
| 6,159,005 A | 12/2000 | Herold |
| 6,730,156 B1 | 5/2004 | Windisch |
| 8,329,776 B2 | 12/2012 | Hecht |
| 9,782,329 B2 | 10/2017 | Hecht |
| 11,267,968 B2 * | 3/2022 | Osswald ................ B33Y 70/00 |
| 12,071,544 B2 * | 8/2024 | Hoffmann ............... G03F 7/027 |
| 2004/0124396 A1 | 7/2004 | Flynn |
| 2005/0027032 A1 | 2/2005 | Hare |
| 2007/0015864 A1 | 1/2007 | Hintzer |
| 2007/0015937 A1 | 1/2007 | Hintzer |
| 2007/0025902 A1 | 2/2007 | Hintzer |
| 2007/0049652 A1 * | 3/2007 | Ito .......................... B33Y 70/00 522/148 |
| 2007/0065770 A1 | 3/2007 | Lubbers |
| 2007/0276068 A1 | 11/2007 | Hintzer |
| 2010/0304338 A1 | 12/2010 | Cramer |
| 2012/0077142 A1 | 3/2012 | Maurer |
| 2013/0130192 A1 | 5/2013 | Schmitt |
| 2015/0202032 A1 | 7/2015 | Benz |
| 2016/0244625 A1 | 8/2016 | Clapp |

FOREIGN PATENT DOCUMENTS

| | | |
|---|---|---|
| EP | 0173085 | 3/1986 |
| EP | 0231420 | 9/1991 |

(Continued)

OTHER PUBLICATIONS

Cole, "Synthesis and Characterization of Thiol-Ene Functionalized Siloxanes and Evaluation of Their Crosslinked Network Properties", Journal of Polymer Science Part A: Polymer Chemistry 2012, vol. 50, pp. 4323-4333.
Kugel, "Investigation of a New Approach to Measuring Contact Angles for Hydrophilic Impression Materials", Journal of Prosthodontics, Mar.-Apr. 2007, vol. 16, No. 2, pp. 84-92.
International Search Report for PCT International Application No. PCT/IB2020/055409, mailed on Sep. 3, 2020, 5 pages.

*Primary Examiner* — Michael F Pepitone

(57) ABSTRACT

The invention relates to a process of taking a dental impression, the process comprising the steps of providing a radiation-curable dental impression composition, placing the radiation-curable dental impression composition in contact with dental tissue, applying radiation to the radiation-curable dental impression composition, letting the radiation-curable dental impression composition cure, removing the cured dental impression composition from the dental tissue, the radiation-curable dental impression composition comprising mercapto-functional polyorganosiloxane(s), VQM resin(s), photo-initiator(s) for initiating a curing reaction between, and optionally filler(s). The invention also relates to a cured dental impression obtained by radiation curing the radiation-curable dental impression composition, a kit of parts containing the radiation-curable dental impression composition and a dental impression tray filled with the radiation-curable dental impression composition.

12 Claims, No Drawings

(56) References Cited

FOREIGN PATENT DOCUMENTS

| | | |
|---|---|---|
| EP | 2442778 | 4/2012 |
| EP | 3470049 | 4/2019 |
| WO | WO 1996-032088 | 10/1996 |
| WO | WO 2004-060964 | 7/2004 |
| WO | WO 2007-140091 | 12/2007 |
| WO | WO 2018-085744 | 5/2018 |
| WO | WO 2018-136351 | 7/2018 |
| WO | WO 2019-150256 | 8/2019 |
| WO | WO 2020-170114 | 8/2020 |

* cited by examiner

PROCESS OF TAKING A DENTAL IMPRESSION WITH A RADIATION-CURABLE COMPOSITION CONTAINING MERCAPTO-FUNCTIONAL POLYORGANOSILOXANES AND VQM RESINS

CROSS REFERENCE TO RELATED APPLICATIONS

This application is a national stage filing under 35 U.S.C. 371 of PCT/IB2020, filed Jun. 9, 2020, which claims the benefit of European Application No. 19179611.9, filed Jun. 12, 2019, the disclosure of which is incorporated by reference in its/their entirety herein.

FIELD OF INVENTION

The invention relates to a process of taking a dental impression by using a radiation-curable dental impression composition comprising mercapto-functional polyorganosiloxane(s), VQM resin(s), photo-initiator(s) for initiating a curing reaction and optionally filler(s).

The invention also relates to a kit of parts comprising such a radiation-curable silicone dental impression composition and the following parts alone or in combination: dental impression, tray, light-curing device, crown and bridge material, dental retraction material.

BACKGROUND

Commercially available dental impression compositions are typically provided as a base/catalyst system. Different kinds of dental impression compositions are available.

There are dental impression compositions which contain polyvinyl polyorganosiloxane components and cure by hydrosilylation reaction using a platinum catalyst. These compositions are typically referred to as VPS dental impression materials.

There are also dental impression compositions which contain aziridino-functional polyether components. The curing of these compositions is typically initiated by using adequate Lewis acids. These compositions are typically referred to as polyether dental impression materials.

For use, the respective pastes of these dental impression compositions need to be mixed before use. Upon mixing the curing reaction starts. Thus, the time available to the practitioner for taking a dental impression (working time) is limited.

It would be desirable to have a dental impression composition where the working time can be chosen freely.

For addressing this need various radiation-curable dental impression compositions have been suggested.

EP 0 173 085 (Harre) describes chain extended urethane diacrylate dental impression materials containing an initiator which can be activated by actinic light.

U.S. Pat. No. 5,100,929 (Jochum et al.) describes a photopolymerizable dental composition which is curable with visible light and which contains polymerizable monomers of the group of the poly-thiol compounds each having at least two thiol groups and polymerizable monomers of the group of the poly-ene compounds each having at least two ethylenically unsaturated groups and at least one photo-initiator, wherein said composition contains respectively related to the sum of all the polymerizable monomers (a) at least 10% by weight of one or more of the poly-thiol compounds, (b) at least 10% by weight of one or more of the poly-ene compounds and (c) as photo-initiator 0.01-5% by weight of at least one acyl phosphine compound.

EP 3 470 049 A1 (Dentsply) describes a dental impression material to be cured by visible light comprising a compound having one or more aliphatic unsaturated groups, a compound containing at least one silicon-bonded hydrogen atom and not having more than three hydrogen atoms attached to any one silicone atom, a photoactivatable catalyst component and a specific initiator component.

US 2010/0304338 (Cramer et al.) describes methods and compositions for single component photo-initiated dental impression materials. The impression material is said to be workable in its pre-cured state and cures rapidly upon exposure to light. The curable impression material contains a polysiloxane-based thiol monomer and a vinyl monomer. It is outlined, that on the one hand the impression material should exhibit improved hydrophilicity before curing and on the other hand decreased hydrophilicity after curing to allow an easier removal of the impression material from the mouth of the patient. It is also outlined that the impression materials should have an appropriate flexibility. The rubbery modulus should be above the glass transition temperature Tg. In Example 6 it is outlined that the rubbery modules increases significantly, if a filler is added.

U.S. Pat. No. 6,046,250 (Boardman et al.) describes a radiation-curable composition comprising polyorganohydrosiloxanes, polyorganosiloxanes, a certain platinum complex and a free-radical photo-initiator. The composition can be used for preparing dental impressions, adhesives, release liners and caulking materials.

Cole and Bowman report on "Synthesis and Characterization of Thiol-en Functionalized Siloxanes an Evaluation of Their Crosslinked Network Properties" in Journal of Polymer Science Part A: Polymer Chemistry 2012, 50, 4323-4333.

WO 2018/136351 A1 (3M) relates to a curable composition for dental retraction comprising a resin matrix comprising at least one polyorganosiloxane with at least two olefinically unsaturated groups as component A1, at least one organohydrogenpolysiloxane as component A2, optionally at least one vinyl functional QM silicone component as component A3, at least one alkylsiloxane having at least one carbinol, silanol, or alkoxy moiety as component B, optionally surfactant(s) as component E, optionally additive(s) as component F, a filler system comprising filler(s) as component D, a catalyst system comprising addition cure catalyst component C-A suitable to cure components A1 and A2, condensation cure catalyst component C-B suitable to cure component B.

However, the solutions proposed in the prior art are not fully satisfying. The physical-mechanical properties of the cured composition obtained from radiation-curable dental impression materials are often not considered sufficient.

SUMMARY OF INVENTION

Thus, there is still a need for a dental impression material which is curable on demand, that is, at a time the practitioner considers to be appropriate. The dental impression material should also be easy to manufacture and use.

Further, the curing of the dental impression material should be sufficiently fast and complete and allow for the curing of the material also in thicker layers. In this respect, it can be desirable, if the material is sufficiently transparent.

Ideally, the dental impression obtained after curing should have adequate mechanical properties such as sufficient tensile strength and/or elongation at break.

One or more of the above objects are addressed by the invention described in the present text and claims.

In one embodiment the invention features a process of talking a dental impression, the process comprising the steps of
- providing a radiation-curable dental impression composition,
- placing the radiation-curable dental impression composition in contact with dental tissue,
- applying radiation to the radiation-curable dental impression composition,
- letting the radiation-curable dental impression composition cure,
- removing the cured dental impression composition from the dental tissue,
- the radiation-curable dental impression composition comprising
   - mercapto-functional polyorganosiloxane(s) as Component A,
   - VQM resin(s) as Component B1,
   - photo-initiator(s) as Component C for initiating a curing reaction between Component A and Component B1,
   - optionally filler(s) as Component D, as described in the present text and claims.

In another embodiment, the invention relates to a cured dental impression being characterized by the following features alone or in combination: being rubber-elastic; having a Shore hardness A of 30 to 90, having a tensile strength of 1.0 to 50 MPa, having an elongation at break of 80 to 1,000%, having a water-contact angle equal to or smaller than 90 as described in the present text and claims.

A further embodiment of the invention is directed to a kit of part comprising the radiation-curable dental impression composition as described in the present text and claims, and the following parts alone or in combination: dental impression tray, light-curing device, crown and bridge material, dental retraction material.

In yet a further embodiment, the invention relates to a dental impression tray filled with the radiation-curable dental impression material described in the present text and claims.

Unless defined differently, for this description the following terms shall have the given meaning:

"Elastomeric" means rubber-elastic or rubber-like. Elastomeric materials can be characterized e.g. by a certain tensile strength and/or elongation at break. Other means for characterizing elastomeric materials include the measurement e.g. of the Young's modulus. Elastomeric materials typically have an E-modulus in the range from 0.8 to 10 MPa or from 1 to 8 MPa or from 1.5 to 6 MPa (determined e.g. according to DIN 53504, thickness of sample: 2 mm).

A "hardenable component or material" (e.g., "polymerizable component" or "crosslinkable component") is any component which can be cured or solidified e.g., by heating to cause polymerization, chemical crosslinking, radiation-induced polymerization or crosslinking by using a redox initiator. A hardenable component may contain, for example, only one, two, three or more polymerizable groups. The term "compound" or "component" is a chemical substance which has a certain molecular identity or is made of a mixture of such substances, e.g., polymeric substances.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

"Polymer" or "polymeric material" are used interchangeably to refer to a homopolymer, copolymer, terpolymer etc.

"Poly" means that the respective substance contains at least 10 repeating units of a certain monomer moiety.

As used herein, "(meth)acryl" is a shorthand term referring to "acryl" and/or "methacryl". For example, a "(meth)acryloxy" group is a shorthand term referring to either an acryloxy group (i.e., $CH_2=CH-C(O)-O-$) and/or a methacryloxy group (i.e., $CH_2=C(CH_3)-C(O)-O-$).

The terms "vulcanizing", "hardening", "polymerizing", "crosslinking", "curing" and "setting" are used interchangeable and refer to compositions that have as a common attribute the development of a crosslinked polymer from relatively low molecular weight linear or branched polymers or pre-polymers by means of a chemical reaction that simultaneously forms these crosslinks and effectively extends chain length at room temperature.

"Room temperature curable" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods. The compositions of the invention are room temperature vulcanizing.

A "powder" means a dry, bulk material composed of a large number of fine particles that may flow freely when shaken or tilted.

A "particle" means a substance being a solid having a shape which can be geometrically determined. The shape can be regular or irregular. Particles can typically be analysed with respect to e.g. particle size and particle size distribution. A particle can comprise one or more crystallites. Thus, a particle can comprise one or more crystal phases.

By "paste" is meant a soft, viscous mass of solids dispersed in at least one liquid or a soft, viscous mass of a polymer.

A "photo-initiator" is a substance being able to start or initiate the curing process of a hardenable composition in the presence of radiation, in particular light (wave length of 300 to 700 nm).

"Surfactants" are agents which are able to lower the surface tension of water. If desired, the effect of lowering the surface tension of water can be measured by determining the water-contact angle.

"Dental compositions" are typically hardenable compositions, which can be hardened at ambient conditions, including a temperature range of 15 to 50° C. or 20 to 40° C. within a time frame of 30 min or 20 min or 10 min. Higher temperatures are not recommended as they might cause pain to the patient and may be detrimental to the patient's health.

Dental compositions are typically provided to the practitioner in comparable small volumes, that is volumes in the range of 0.1 to 500 ml or 0.5 to 100 ml or 1 to 50 ml. Thus, the storage volume of useful packaging devices is within these ranges.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is typically carried out by placing a viscous material into the mouth in a customised or stock tray. The material then sets to become an elastic solid, and when removed from the mouth retains the shape of the teeth and gingiva.

A "dental impression composition" is a composition or material used for making impressions of the tooth structure. A dental impression material is usually applied on a dental impression tray. A dental impression material can be based on different chemical substances and crosslink by various chemical reactions. Common materials used for dental impressions include alginate, agar, polyethers including aziridine substituted polyether materials as well as silicones, both condensation-cured silicones and addition-cured silicones including polyvinyl siloxanes (so-called VPS materials).

The term "dental impression composition" comprises precision impression materials, situation impression materials, bite registration materials, duplicating materials (applicable for the duplication of master models, e.g. for all-ceramic restorations requiring a refractory investment model and when inlays, onlays, cantilevers and other precision attachments are being fabricated) and modelling materials (applicable for e.g. reconstructing the gingival, producing crowns and bridges).

A "putty like dental impression material" is a kneadable dental impression material having a consistency of 35 mm or below according to ISO 4823:2015-08.

A "dental retraction material" is a material intended to be placed in the gingival sulcus, that is, the natural space between the hard dental tissue (i.e. tooth structure) and the gum tissue that surrounds the hard dental tissue. Once placed in the gingival sulcus, the dental retraction material will exert pressure on the surrounding tissue resulting in a widening of the gingival sulcus to enable the practitioner to get a more precise impression of the dental situation below the gum line during a dental impression process. Like a dental impression material, a dental retraction material is removed from the mouth of the patient after use.

The term "dental tissue" includes the hard tooth substance (enamel and dentin), the gingival region (soft dental tissue) surrounding the hard tooth substance and hard tooth substance bearing orthodontic appliances.

A "(temporary) crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to 6 days), a few weeks (1 to 4 weeks) or a few months (1 to 6 month).

A "surfactant" is an agent imparting wettability to a material, that is making the material more wettable compared to a material not containing a surfactant. The wettabilty can be determined by the water contact angle which can be measured using e.g. a goniometer DSA 10 (Kruss). A low water contact angle indicates a better wettability.

"Molecular weight" in the context of the invention and if not otherwise indicated always means number average molecular weight ($M_n$). The molecular weight ($M_n$) of the polymerizable compound before setting can be determined using nuclear magnetic resonance spectroscopy (end-group determination). In this respect proton ($^1$H) NMR techniques are employed to estimate the molecular weight of the precursor of the prepolymer. Integrated signals of the terminal —$CH_2$— groups are compared to the integrated sum of proton signals from backbone hydrocarbon protons taking into account co-monomer ratio, if applicable. To achieve appropriate separation of terminal methylene proton signals from the backbone proton signals, terminal hydroxyl groups are esterified with trifluoroacetic acid.

A material or composition is "essentially or substantially free of" a certain component within the meaning of the invention, if the material or composition does not contain said component as an essential feature. Thus, said component is not willfully added to the composition or material either as such or in combination with other components or ingredient of other components. Ideally the composition or material does not contain the said component at all. However, sometimes the presence of a small amount of the said component is not avoidable e.g. due to impurities.

"Ambient conditions" mean the conditions which the composition described in the present text is usually subjected to during storage and handling. Ambient conditions may, for example, be a pressure of 900 to 1100 mbar, a temperature of 10 to 40° C. and a relative humidity of 10 to 100%. In the laboratory, ambient conditions are typically adjusted to 20 to 25° C. and 1000 to 1025 mbar.

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and used in the specification and claims are to be understood as number as such and also as being modified by the term "about."

The term "about" can allow for a degree of variability in a value or range, e.g. within 10% or within 5% or within 1% of a given value or a given limit of a range.

The terms "comprise" or "contain" and variations thereof do not have a limiting meaning where these terms appear in the description and claims. "Consisting essentially of" means that specific further components can be present, namely those which do not materially affect the essential characteristic of the article or composition. "Consisting of" means that no further components should be present. The term "comprise" shall include also the terms "consist essentially of" and "consists of".

"And/or" means one or both. E.g., the expression component A and/or component B refers to a component A alone, component B alone, or to both component A and component B.

DETAILED DESCRIPTION

It has been found that the composition described in the text has a couple of advantageous properties.

The radiation-curable dental impression composition described in the present text is easy to manufacture. Essentially, the production can be done by simply mixing the components of the composition.

The radiation-curable dental impression composition is also easy to use. The composition can either be applied to a dental impression tray, which is then put in the mouth of a patient. Alternatively, the composition can be directly applied to the dental tissue and irradiated.

As the dental impression composition is radiation-curable, the curing can be initiated at any time ("on demand") by simply applying radiation of an appropriate wave length, including visible light.

This allows to easily adjust the working time which is needed by the practitioner to simultaneously capture the negative image of different dental situations in the mouth of a patient.

If only a small region of the dental situation needs to be captured, the time needed for curing can be reduced as the curing is initiated by radiation and not by mixing two different components or parts.

As there is no working time which has to be kept in mind, the practitioner can work without time-pressure which typically results in dental impressions having a better quality (e.g. less defects).

It was also found that once the curing process has been initiated the crosslinking of mercapto-functional polyorganosiloxane and VQM resins proceeds very fast.

To ensure the curing of the whole curable composition, a sufficient depth of cure is typically desired and/or needed. Otherwise, there remains the risk that uncured material remains. This is not only very uncomfortable for the patient but also negatively affects the quality of the dental impression, which later is to be used for preparing a dental restoration (e.g. temporary crown or bridge).

It was found that the depth of curing of dental impression compositions can be improved, if VQM resins are used in combination with mercapto-functional polyorganosiloxane(s).

Thus, not only a sufficiently fast but also complete curing can be achieved. This allows for the curing of the dental impression composition in thicker layers.

A sufficient depth of curing is important for a radiation-curing dental impression material which is typically used together with a light-emitting dental impression tray, since all of the radiation-curable material needs to be cured within a short time frame.

As the dental impression composition can be formulated as a 1-part composition, there is also no need for storing the composition in two containers or compartments to be stored separately before use. There is also no need for an additional mixing step before use of the dental impression composition.

The invention provides a process of taking a dental impression of the dental situation in the mouth of a patient by using a radiation-curable dental impression material having an adequate viscosity and which can be cured in thick layers and having good mechanical properties (such as tensile strength) after curing.

The invention relates to process of taking a dental impression by using a radiation-curable dental impression composition as described in the present text.

The radiation-curable dental impression composition can typically be characterized by the following features alone or in combination:
a) being a paste;
b) having a consistency of 1, 2 or 3 according to ISO 4823:2017;
c) having a viscosity of 1 to 100 Pa*s at 23° and 50 s$^{-1}$;
d) having a depth of cure of 2 to 8 mm according to DIN EN ISO 6874:2015.

A combination of the following features is sometimes preferred: a) and d); orb) and d); or c) and d); or b), c) and d).

If desired, the respective properties can be determined as described in the example section.

The radiation-curable dental impression composition comprises mercapto-functional polyorganosiloxane(s) as Component A.

It was found that by using mercapto-functional polyorganosiloxane(s) in combination with VQM resins, the depth of curing of the radiation-curable dental impression composition can be improved.

A mixture or dispersion of VQM resins in organosiloxanes (like those described further down below) is typically milky cloudy and is thus scattering the light.

Without wishing to be bound to a particular theory, it is believed that light-scattering helps to diffuse the light applied by a radiation source such as a dental curing light also to those regions of the radiation-curable dental impression material, which are not directly irradiated.

The mercapto-functional polyorganosiloxane(s) is typically characterized by the following features alone or in combination:
a) fraction of (mercaptoalkyl)methylsiloxane units: 7 to 100 mol % or 45 to 100 mol % or 70 to 100 mol %;
b) molecular weight (Mn): 500 to 20,000 g/mol or 600 to 15,000 g/mol;
c) viscosity: 10 to 1,000 mPa*s or 20 to 750 mPa*s at 23° C.

Mercapto-functional polyorganosiloxanes having a fraction of (mercaptoalkyl)methylsiloxane units in the range of 45 to 100 or 70 to 100 mol % are sometimes preferred.

If desired, the molecular weight can be determined by gel permeation chromatography (GPC) using an appropriate solvent and an appropriate polystyrene standard.

The mercapto-functional polyorganosiloxane is typically characterized by the following formula (1):

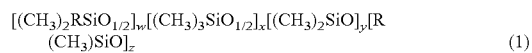

$$[(CH_3)_2RSiO_{1/2}]_w[(CH_3)_3SiO_{1/2}]_x[(CH_3)_2SiO]_y[R(CH_3)SiO]_z \qquad (1)$$

with w being from 0 to 0.1, x being from 0 to 0.1 and w+x being from 0.01 to 0.1; y being from 0 to 0.93, z being from 0.07 to 0.99, wherein each R is independently selected from a mercapto $C_{1-10}$ hydrocarbyl group.

These mercapto-functional polyorganosiloxanes typically comprise a high amount of mercapto moieties (e.g. in the range of 45 to 100 or 70 to 100 mol %).

Examples of mercapto-functional polyorganosiloxanes include poly(mercaptobutyl)methylsiloxane, poly(mercaptopropyl)methylsiloxane, poly(mercaptoethyl)methylsiloxane, poly(mercaptomethyl)methylsiloxane, co-poly(mercaptopropyl)methylsiloxane dimethylsiloxane and mixtures thereof.

In addition to polyorganosiloxanes comprising a high amount of mercapto moieties, the composition can also comprise polyorgansiloxane with a low amount of mercapto moieties.

Using a mixture of two different mercapto-functional polyorgansiloxanes may help to adjust the Shore hardness of the cured composition. In addition, it has been observed that by using a mixture of two different mercapto-functional polyorgansiloxanes the optical properties (such as e.g. transparency) of the composition can be adjusted.

Such polyorgansiloxane with a low amount of mercapto moieties are for example mercaptopropyldimethyl siloxoy end-capped polydimethylsiloxanes or copolymers according to formula (2):

$$[(CH_3)_2RSiO_{1/2}]_a[(CH_3)_2SiO]_b \qquad (2)$$

with a=0.02-0.03 and R being a mercapto $C_{1-10}$ hydrocarbyl group.

These polyorganosiloxanes typically comprise 2 to 3 mol % of mercaptopropyldimethylsiloxy units.

Component A is typically present in the following amounts:
Lower amount: at least 0.5 or at least 1 or at least 2 wt. %;
Upper amount: at most 50 or at most 45 or at most 40 wt. %;
Range: 0.5 to 50 or 1 to 45 wt. % or 2 to 40 wt. %;
wt. % with respect to the weight of the whole composition.

The radiation-curable dental impression composition comprises VQM resins.

Using VQM resins can be beneficial as these components may not only help to improve the depth of cure, but also mechanical properties like tensile strength.

QM resins comprise as Q a quadrifunctional $SiO_{4/2}$ unit and as M building blocks such as monofunctional units $R_3SiO_{1/2}$, wherein R is independently selected from vinyl, methyl, ethyl or phenyl or tri- or bi-functional units.

An example of a VQM resin which can be used has the structure according to formula (3):

$$Si[O-Si(CH_3)_2-CH=CH_2]_4 \qquad (3)$$

Examples of suitable VQM resins are e.g. described in US 2005/0027032 (Hare). The content of this document with respect to the description of QM resins is herewith incorporated by reference.

In one embodiment, it is preferred to use a dispersion of VQM resin(s) in vinylfunctional organopolysiloxanes. These liquids are later described as Component B2.

According to one embodiment, the dispersion of the organosiloxane with at least two aliphatic unsaturated carbon-carbon moieties having a VQM structure is characterized by the following features alone or in combination:
a) viscosity: 500 to 90,000 mPa*s or 550 to 85,000 mPa*s or 600 to 80,000 mPa*s at 23° C.;
b) concentration of unsaturated moieties: at least 0.15 mmol/g or in the range of 0.15 to 0.80 mmol/g.

More precisely, the dispersion of the organosiloxane with at least two aliphatic unsaturated carbon-carbon moieties having a VQM structure is characterized by the following features in combination:
a) viscosity: 500 to 90,000 mPa*s; and
b) concentration of unsaturated moieties: at least 0.15 mmol/g.

A high concentration of unsaturated moieties may help to further improve mechanical properties like tensile strength.

VQM resins are typically present in the following amounts:
Lower amount: at least 10 or at least 15 or at least 20 wt. %;
Upper amount: at most 60 or at most 55 or at most 50 wt. %;
Range: 10 to 60 or 15 to 55 wt. % or 20 to 50 wt. %;
wt. % with respect to the weight of the whole composition.

The radiation-curable dental impression composition may also comprise organosiloxane(s) with at least two aliphatic unsaturated carbon-carbon moieties not being a VQM resin as component B2.

According to one embodiment, the organosiloxane with at least two aliphatic unsaturated carbon-carbon moieties has a linear structure.

According to one embodiment, the organosiloxane with at least two aliphatic unsaturated carbon-carbon moieties having a linear structure is characterized by the following features alone or in combination:
a) Molecular weight (Mn): 250 to 200,000 g/mol or 500 to 175,000 g/mol;
b) Viscosity: 1 to 90,000 mPa*s or 2 to 20,000 mPa*s or 10 to 10,000 mPa*s at 23° C.

Typically, the organosiloxane(s) with at least two aliphatic unsaturated carbon-carbon moieties is an organopolysiloxane with at least two pendant or terminal triorganosiloxy groups in which at least one of the three organic groups is a group with an ethylenically unsaturated double bond.

Generally, the groups with an ethylenically unsaturated double bond can be located on any monomeric unit of the organopolysiloxane. It is, however, preferred, that the groups with an ethylenically unsaturated double bond are located on or at least near the terminal, monomeric units of the polymer chain of the organopolysiloxane. In another embodiment, at least two of the groups with an ethylenically unsaturated double bond are located on the terminal monomeric units of the polymer chain.

The term "monomeric units" relates to repeating structural elements in the polymer that form the polymer backbone, unless expressly stated otherwise.

One group of organosiloxane can be represented by formula (4):

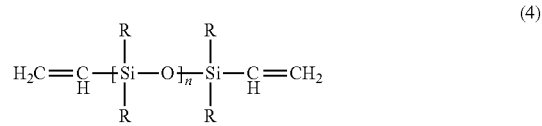

in which the radicals R, independently from each other, represent a non-substituted or substituted, monovalent hydrocarbon group with 1 to about 6 C atoms, which is preferably free from aliphatic multiple bonds and where n generally can be chosen such that the viscosity of the polyorganosiloxane lies in the range of 1 to 90,000 mPa*s or 2 to 20,000 or 10 to 10,000 mPa*s. The parameter n can, e.g., be in the range of 3 to 10,000 or 5 to 5,000.

Generally, the radical R in the above formula can independently represent any non-substituted or substituted, monovalent hydrocarbon group with 1 to 6 C atoms. Non-substituted or substituted, monovalent hydrocarbon groups with 1 to 6 C atoms can be linear or, if the number of carbon atoms exceeds 2, branched or cyclic. Generally, the radical R can be equipped with any type of substituent or substituents provided they do not interfere with any other constituents or substituents of the composition and do not interfere with the curing reaction.

The term "interfere" as used in the context of the present text relates to any influence of such a substituent on at least one of the other substituents or constituents of the composition or the curing reaction, or both, which might be detrimental to the properties of the hardened product.

The term "detrimental" as used in the context of the present text relates to a change of properties of the precursors or the cured product that negatively affect the usefulness of the precursors or the cured product in their intended use.

In another embodiment, at least 50% of the radical(s) R are methyl groups. Examples of other radicals R that can be present in the polyorganosiloxane according to the above formula are ethyl, propyl, iso-propyl, n-butyl, iso-butyl, tert-butyl, the pentyl isomers, the hexyl isomers, vinyl, allyl, propenyl, iso-propenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or heteroaromatic groups like phenyl or substituted phenyl groups.

Examples for such molecules are described in U.S. Pat. No. 4,035,453 (Hittmaier et al.), the disclosure of which, especially regarding the above-mentioned molecules, their chemical constitution and their preparation, is regarded as being part of the disclosure of the present document and is included herein by reference.

Particularly preferred are linear polydimethylsiloxanes according to the above formula having viscosities within the specified viscosity ranges and end groups comprising dimethylvinylsiloxy units and methyl groups as the radical(s) R.

A Component B2 which can be employed can consist of one type of organosiloxane.

The organosiloxane can have a viscosity starting in the range of 1 to 90,000 mPa*s, or 5 to 20,000 mPa*s or 10 to 10,000 mPa*s.

It is, however, also possible that Component B2 comprises two or more constituents, B2a, B2b and so on, which can differ, e.g., in the chemical composition of their backbone, or their molecular weight, or their substituents or their viscosity, or any other differentiating feature or two or more of the above-mentioned features.

In one embodiment, the difference in viscosities of different constituents of Component B2x can be higher than a factor of 2, e.g., higher than a factor of 5, higher than a factor of 10, higher than a factor of 20, higher than a factor of 30, higher than a factor of 40, higher than a factor of 50, higher than a factor of 60, higher than a factor of 70, higher than a factor of 80, higher than a factor of 90 or higher than a factor of 100. The difference in viscosities can be even higher, e.g., higher than a factor of 200, higher than a factor of 300, higher than a factor of 500, higher than a factor of 800, higher than a factor of 1,000 or higher than a factor of 5,000, it should, however, preferably not exceed a value higher than a factor of 10,000. It should be kept in mind that the values mentioned above relate to a factor for the difference in viscosities, not the viscosity values themselves.

If present, the organosiloxane(s) with at least two aliphatic unsaturated carbon-carbon moieties as Component B2 is typically present in the following amounts:

Lower amount: at least 10 or at least 20 or at least 30 wt. %;
Upper amount: at most 70 or at most 65 or at most 60 wt. %;
Range: 10 to 70 or 20 to 65 wt. % or 30 to 60 wt. %; wt. % with respect to the weight of the whole composition.

Sometimes it can be preferred to use a mixture of organosiloxane(s), in particular a mixture of organosiloxane(s) with at least two aliphatic unsaturated carbon-carbon moieties having a linear structure, e.g. according to formula (4), and dispersion(s) of organosiloxanes having a VQM structure.

If a mixture is used, the ratio of organosiloxanes according to formula (4)/organosiloxanes having a VQM structure is typically in a range of 1 to 4 to 4 to 1, or 1 to 2 to 2 to 1 with respect to weight.

The radiation-curable dental impression composition described in the present text comprises one or more photo-initiator(s) as Component C.

The nature and structure of the photo-initiator is not particularly limited, unless the desired result cannot be achieved.

Using a photo-initiator being soluble in the radiation-curable resin composition of the present text is preferred.

The photo-initiator is capable of generating free radicals for polymerization upon exposure to light.

The photo-initiator(s) has typically a light absorption band in a wave length range of 390 to 500 nm.

The following class of photo-initiator(s) was found to be useful: one-component system where two radicals are generated by cleavage.

In one embodiment, blends of at least two different photo-initiators are used.

Photo-initiators which can be used typically contain a moiety selected form benzoin ether, acetophenone, benzoyl oxime or acyl phosphine oxids, phenylglyoxate, □-hydroxyketones or □-aminoketones.

Exemplary UV initiators include 1-hydroxycyclohexyl benzophenone (available, for example, under the trade designation "OMNIRAD™ 184" from IGM Resin B.V., Waalwijk, Netherlands), 4-(2-hydroxyethoxy)phenyl-(2-hydroxy-2-propyl) ketone (available, for example, under the trade designation "OMNIRAD™ 2959" from IGM Resin B.V), 2-hydroxy-2-methylpropiophenone (available, for example, under the trade designation "OMNIRAD™ 1173" from IGM Resin B.V.) and 2-benzyl-2-(N,N-dimethylamino)-1-(4-morpholinophenyl)-1-butanone (OMNIRAD™ 369, IGM Resins B.V.).

A particularly suitable class of photo-initiators include the class of acylphosphine oxides, as described e.g. in U.S. Pat. No. 4,737,593 (Elrich et al.).

Such acylphosphine oxides can typically be characterized by formula (5)

$$(R^9)_2-P(=O)-C(=O)R^{10} \qquad (5)$$

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S—, O—, or N-containing five- or six-membered heterocyclic group, or a $Z-C(=O)-P(=O)-(R^9)_2$ group, wherein Z represents a divalent hydrocarbyl group such as alkylene or phenylene having 2 to 6 carbon atoms.

Preferred acylphosphine oxides are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms.

A preferred acylphosphine oxide is bis(2,4,6-trimethylbenzoyl)phenyl phosphine oxide (OMNIRAD™ 819, IGM Resin B.V., Waalwijk, Netherlands).

In another embodiment, it is preferred to use liquid blends of acylphosphine oxides with at least one other photo-initiator (available e.g. as OMNIRAD™ 1000, OMNIRAD™ 2022, OMNIRAD™ 2100 or OMNIRAD™ 4265, IGM Resin B.V., Waalwijk, Netherlands).

Tertiary amine reducing agents may be used in combination with an acylphosphine oxide.

Illustrative tertiary amines include ethyl 4-(N,N-dimethylamino)benzoate and N,N-dimethylaminoethyl methacrylate.

Suitable are also photo-initiator systems containing a sensitizer comprising an alpha-alpha di-keto moiety, an anthraquinone moiety, a thioxanthone moiety or benzoin moiety. Sensitizers containing an alpha-alpha di-keto moiety are often preferred.

Typical photo-initiator systems comprise a combination of a sensitizer and a reducing agent, which is often referred to as photo-initiator system.

Examples of sensitizers which can be used include camphorquinone, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthraquinone, 1-methyl-anthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylaminobenzophenone.

As the reducing agent or donor component, tertiary amines and the like are generally used. Suitable examples of the tertiary amines include N,N-dimethyl-p-toluidine, N,N-dimethylaminoethyl methacrylate, triethanolamine, methyl 4-dimethylaminobenzoate, ethyl 4-dimethylaminobenzoate, methyldiphenylamine and isoamyl 4-dimethylaminobenzoate.

The photo-initiator(s) is typically present in the following amounts:
Lower amount: at least 0.01 or at least 0.05 or at least 0.1 wt. %;
Upper amount: at most 8 or at most 5 or at most 4 wt. %;
Range: 0.01 to 8 or 0.01 to 5 wt. % or 0.01 to 4 wt. %;
wt. % with respect to the weight of the whole composition.

The radiation-curable dental impression composition described in the present text does not need to contain a filler.

However, certain embodiments of the radiation-curable dental impression composition described in the present text comprise filler(s) as Component D.

If present, the nature and structure of the filler(s) are not particularly limited as far as the desired results can be achieved.

If present, the filler(s) is typically present in either of the following amounts:
Lower limit: at least 5 or at least 10 or at least 12 wt. %;
Upper limit: utmost 60 or utmost 50 or utmost 40 wt. %;
Range: 5 to 60 or 10 to 50 or 12 to 40 wt. %;
wt. % with respect to the weight of the dental composition.

Reinforcing and non-reinforcing filler(s) can be used.

Reinforcing fillers typically contain nano-sized particles.

The reinforcing filler(s) can be selected from aggregated, agglomerated or discrete (i.e. non-agglomerated, non-aggregated) nano-sized particles or mixtures thereof.

It was found that compared to other fillers, using nano-filler(s) can be beneficial, because it allows for the formulation of a composition with high filler load resulting typically in better mechanical properties.

According to one embodiment, the radiation-curable composition may comprise aggregated nano-sized particles.

The filler comprising aggregated nano-sized particles can typically be characterized by at least one or all of the following features:
Specific surface (BET according to Brunauer, Emmet and Teller): 30 to 400 or 60 to 300 or 80 to 250 m$^2$/g;
comprising particles of $SiO_2$, $ZrO_2$, $Al_2O_3$ and mixtures thereof.

If desired, the specific surface can be determined according to Brunauer, Emmet and Teller (BET; e.g. by using a device like Monosorb™ available from Quantachrome).

A suitable filler comprising aggregated nano-sized particles can be produced according to the processes described e.g. in U.S. Pat. No. 6,730,156 (Windisch et al.) (preparatory example A).

A useful filler comprising aggregated nano-sized particles can be prepared from a suitable sol and one or more oxygen containing heavy metal compound solution(s) precursors which may be salts, sols, solutions, or nano-sized particles; of these, sols are preferred.

The resulting fillers comprise, contain, consist essentially or consist of aggregated nano-sized particles. If desired, this can be proven by transmission electron microscopy (TEM).

If desired, the surface of the filler particles can be surface treated. The surface-treatment can be accomplished according to a process as described in U.S. Pat. No. 6,730,156 (Windisch et al.) (e.g. preparatory example B).

If present, the filler comprising aggregated nano-sized particles is typically present in either of the following amounts:
Lower limit: at least 0.1 or at least 0.5 or at least 1 wt. %;
Upper limit: utmost 15 or utmost 12 or utmost 10 wt. %;
Range: 0.1 to 15 or 0.5 to 12 or 1 to 10 wt. %;
wt. % with respect to the weight of the dental composition.

According to one embodiment, the filler(s) may comprise agglomerated nano-sized particles.

Nano-filler(s) comprising agglomerated nano-sized particles are typically characterized by at the following features alone or in combination:
Specific surface: (BET according to Brunauer, Emmet and Teller): 30 to 400 or 50 to 300 or 70 to 250 m$^2$/g;
comprising particles of $SiO_2$, $ZrO_2$, $Al_2O_3$ and mixtures thereof.

Suitable agglomerated nanoparticles include fumed silicas such as products sold under the tradename Aerosil™ e.g. Aerosil™ OX-130, -150, and -200, Aerosil™ R8200 available from Evonik, (Essen, Germany), CAB-O-SIL™ M5 available from Cabot Corp (Tuscola, Ill.), and HDK™, e.g. HDK-H 2000, HDK H15; HDK H18, HDK H20 and HDK H30 available from Wacker.

If present, agglomerated nano-sized particles are typically present in either of the following amounts:
Lower limit: at least 0.1 or at least 0.5 or at least 1 wt. %;
Upper limit: utmost 15 or utmost 12 or utmost 10 wt. %;
Range: 0.1 to 15 or 0.5 to 12 or 1 to 10 wt. %;
with respect to the weight of whole composition.

According to one embodiment, the filler(s) may comprise discrete nano-sized particles.

Discrete nano-sized particles which can be used are preferably substantially spherical and substantially non-porous.

Filler(s) comprising discrete nano-sized particles are typically characterized by at least one or all of the following features:
Average particle diameter: less than 200 nm or less than 100 nm; comprising particles of $SiO_2$, $ZrO_2$ and mixtures thereof.

Preferred nano-sized silicas are commercially available from Nalco Chemical Co. (Naperville, Ill.) under the product designation NALCO™ COLLOIDAL SILICAS. For example, preferred silica particles can be obtained from using NALCO™ products 1040, 1042, 1050, 1060, 2327 and 2329.

If present, the discrete nano-sized particles are typically present in either of the following amounts:
Lower limit: at least 0.1 or at least 0.5 or at least 1 wt. %;
Upper limit: utmost 15 or utmost 12 or utmost 10 wt. %;
Range: 0.1 to 15 or 0.5 to 12 or 1 to 10 wt. %;
wt. % with respect to the weight of the whole composition.

According to one embodiment, the radiation-curable dental impression composition comprises:
aggregated nano-sized particles in an amount of 0.1 to 15 wt. %,
agglomerated nano-sized particles in an amount of 0.1 to 15 wt. %,
discrete nano-sized particles in an amount of 0.1 to 15 wt. %.

wt. % with respect to the weight of the whole composition.

The above-mentioned fillers can be hydrophobized, for example by treatment with organosilanes or siloxanes or by the etherification of hydroxyl groups to alkoxy groups.

Besides nano-particle filler(s), the composition may also contain filler(s) having a larger particle size. This kind of filler is often referred to as non-reinforcing filler.
The size of the filler particles should be such that a homogeneous mixture can be obtained. The particle distribution is preferably chosen such that there are no fillers with particle sizes of more than 50 μm.

Typically, the size of the non-reinforcing filler particles (d50 value) is below 40 μm or below 10 μm or below 5 μm. Typical ranges (d50 value) include 0.1 to 40 μm or 0.5 to 20 μm or from 1 to 10 μm.

If the filler particles are too small, the viscosity of the resulting composition might increase to a not desirable limit. If the filler particles are too big, the detail accuracy might be negatively affected.

The BET surface of the non-reinforcing filler is typically in a range of 0.05 to 50 m$^2$/g or 0.5 to 30 m$^2$/g or 0.5 to 20 m$^2$/g. Using a filler with a BET surface within this range can be beneficial to adjust the viscosity and tensile strength.

If desired, the BET surface of the filler can be determined as described in DIN 66132. Alternatively, the values for the BET surface are taken from a material data sheet provided by the supplier.

Examples of non-reinforcing fillers include inorganic, hydrophilic or hydrophobic fillers such as silica (quartz, cristobalite), alumina, magnesia, zirconium silicate, inorganic salts (e.g. barium sulphate, calcium carbonate), plaster, and mixtures thereof.

The surface of the non-reinforcing filler can be surface treated, as well, if desired.

Useful fillers are commercially available from companies like Cabot Corporation, Wacker or Degussa under the trade names Aerosil™ (Degussa) HDK™-H (Wacker), Cab-o-Sil™ (Cabot).

If present, reinforcing filler(s) are typically present in either of the following amounts:
Lower limit: at least 0.1 or at least 0.5 or at least 1 wt. %;
Upper limit: utmost 15 or utmost 12 or utmost 10 wt. %;
Range: 0.1 to 15 or 0.5 to 12 or 1 to 10 wt. %;
wt. % with respect to the weight of the whole composition.

The radiation-curable dental impression composition described in the present text may also comprise absorber(s) as component E.

Adding absorber component(s) may help to absorb undesired odour or smell which may be generating during the curing of the radiation-curable composition.

Examples of absorbers which can be used include zeolite(s), molecular sieve(s), cyclodextrine(s) and mixtures thereof.

Suitable molecular sieves, zeolites and silica gel(s) are commercially available from e.g. Evonic company, Zeochem company or UOP company.

Examples of suitable absorbers are marketed under the trade designations Zeolite 3A, Zeolite 4A, Zeolite 5A, Zeolite 13X, Zeolite Y, Sipernat™, Purmol™, Zeoflair etc.

According to one embodiment, the absorber component is characterized by the formula $M^{n+}_{x/n}[(AlO_2)^-_x(SiO_2)_y]$, with n being 1 or 2, M being an alkaline or earth alkaline metal cation, y being from 1 to 150 with y/x being not below 1.

If present, the absorber(s) as Component E is present in the following amounts:
Lower limit: at least 0.1 or at least 0.5 or at least 1 wt. %;
Upper limit: utmost 20 or utmost 15 or utmost 10 wt. %;
Range: 0.1 to 20 or 0.5 to 15 or 1 to 10 wt. %;
wt. % with respect to the weight of the whole composition.

The radiation-curable dental impression composition described in the present text may also comprise stabilizer(s) as Component F.

A stabilizer may extend the shelf life of the curable composition, help prevent undesired side reactions, and adjust the polymerization process of the radiation-curable component(s) present in the radiation-curable composition.

Adding one or more stabilizer(s) to the curable composition may further help to improving the accuracy or detail resolution of the surface of the 3-dim article to be produced.

Stabilizer(s) which can be used often comprise a phenol moiety or phosphonic acid moieties.

Specific examples of stabilizer(s) which can be used include: p-methoxyphenol (MOP), hydroquinone monomethylether (MEHQ), 2,6-di-tert-butyl-4-methyl-phenol (BHT; Ionol), phenothiazine, 2,2,6,6-tetramethyl-piperidine-1-oxyl radical (TEMPO) Vitamin E; N,N'-di-2-butyl-1,4-phenylenediamine; N,N'-di-2-butyl-1,4-phenylenediamine; 2,6-di-tert-butyl-4-methylphenol; 2,4-dimethyl-6-tert-butylphenol; 2,4-dimethyl-6-tert-butylphenol and 2,6-di-tert-butyl-4-methylphenol; 2,6-di-tert-butylphenol; Pentaerythritoltetrakis(3-(3,5-di-tert-butyl-4-hydroxyphenyl)propionate) (previously known as Irganox™ 1010); Octyl-3,5-di-tert-butyl-4-hydroxy-hydrocinnamate; Octadecyl 3-(3,5-di-tert-butyl-4-hydroxyphenyl)propionate; 1,3,5-Trimethyl-2,4,6-tris(3,5-di-tert-butyl-4-hydroxybenzyl) benzene; 2,2,4,4-Tetrakis-tert-butyl-3,3-dihydroxybiphenyl; 4,4-Butylidenebis(6-tert-butyl-m-cresol); 4,4'-Isopropyliden-bis-(2-tert-butylphenol); 2,2'-methylenebis(6-nonyl-p-cresol); 1,3,5-tris(3,5-di-tert-butyl-4-hydroxybenzyl-)-1,3,5-triazine-2,4,6(1H,3H,5H)trione; pyrogallol; N-nitroso-N-phenylhydroxylamine; 3-Propenylphenol, phenothiazine, N-Phenyl-2-naphthylamine, phosphorous acid phenyl-phosphonic acid; vinylphosphonic acid or combinations or mixtures thereof.

Stabilizers which can also be used are selected from the group consisting of organo phosphines, organo-phosphites, organo-phosphonites, di(organo-phosphites), di(organo-phosphonites) and combinations thereof.

Also useful are organophosphorous compounds of the formula $R^1_nP(OR)_{3-n}$ in which n=0, 1, 2 or 3, R=$C_1$-$C_{18}$-alkyl, $C_6$-$C_{30}$-aryl or $C_7$-$C_{31}$-alkylaryl and $R^1$=R or $(CR'_2)_m$ or $(C_6R'_4)_m$ with H=R or OR and m=10.

Especially useful can be, e.g., compounds according to the general formula $P(R)_3$, wherein R can be the same or different and R=$C_1$-$C_{18}$-alkyl, $C_6$-$C_{30}$-aryl, $C_7$-$C_{31}$-alkylaryl, or $OR^1$ with $R^1$=$C_1$-$C_{18}$-alkyl, $C_6$-$C_{30}$-aryl, $C_7$-$C_{31}$-alkylaryl. The radicals R or $R^1$ can be the same or different.

More particular, useful stabilizers include triphenylphosphite (commercially available as Lankromark® LE65 by Akcros Chemicals), diisodecylphenylphosphite (commercially available as Lankromark® LE76 from Akcros Chemicals or as Hostanox® P-EPQ from Clariant), diphenyl-2-ethylhexylphosphite (commercially available as Lankromark® LE98 from Akcros Chemicals), diphenylisodecylphosphite (commercially available as Lankromark® LE131 from Akcros Chemicals), trisnonylphenylphosphite (commercially available as Lankromark® LE109 from Akcros Chemicals), tris(isodecyl)phosphate (commercially available as Lankromark® LE164 from Akcros Chemicals) or tris(tridecyl)phosphate (commercially available as Lankromark® LE406 from Akcros Chemicals) or mixtures of two or more of these compounds.

If present, the stabilizer(s) is present in the following amounts:

Lower amount: at least 0.001 or at least 0.005 or at least 0.01 wt. %;

Upper amount: at most 0.1 or at most 0.1 or at most 1 wt. %;

Range: 0.001 to 1 wt. % or 0.005 to 0.1 wt. %, or 0.01 to 0.1 wt. % with respect to the weight of the curable composition.

The radiation-curable dental impression composition described in the present text may also comprise surfactant(s) as Component G.

Using a surfactant having an HLB value in the range of 3-8 is sometimes preferred.

For non-ionic surfactants, the HLB value can be calculated according to the following formula (Griffin's method): HLB=$20*M_h/M$, with $M_h$ being the molecular mass of the hydrophilic portion of the molecule and M being the molecular mass of the whole molecule.

An HLB value of 0 corresponds to a completely hydrophobic molecule, and a value of 20 corresponds to a completely hydrophilic molecule.

Using a surfactant is sometimes preferred as such a substance can help to dissolve the dye(s) in the radiation-curable composition.

The nature and structure of the surfactant is not particularly limited unless the desired result cannot be achieved.

Surfactants which can be employed can generally be chosen freely from all types of surfactants which improve the hydrophilicity of a silicone moiety containing material (especially, if curable via a hydrosilylation reaction).

Useful surfactants can generally be chosen from anionic, cationic or non-ionic surfactants or mixtures of two or more of such types of surfactants. Using non-ionic surfactants is often preferred.

It can be further preferred, if a mixture of two or more non-ionic surfactants is used.

In certain embodiments, the surfactant or at least one of the surfactants contains a Si-containing moiety, that is, it can be referred to as a Si-containing surfactant.

Suitable examples thereof include hydrophilic silicone oils, which are not capable of being covalently incorporated into the hardened polymer network.

Suitable silicone moieties containing surfactants can be summarized under formula (6)

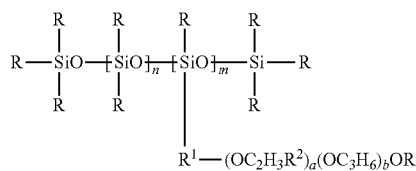

(6)

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and $R^3$ are —$CH_3$, $R^1$ is —$C_3H_6$—, $R^2$ is hydrogen, n is zero or 1, m is 1 to 5, a is 5 to 20 and b is 0.

Several of such ethoxylated surfactants are for example available from Momentive Performance Materials Inc. including "SILWET" surface active copolymers. Preferred surface-active copolymers include Silwet™ 35, Silwet™ L-77, Silwet™ L-7600 and Silwet™ L-7602, Silwet™ L-7608 and Silwet™ Hydrostable 68 and Silwet™ Hydrostable 611. Silwet™ L-77 is an especially preferred ethoxylated surfactant which is believed to correspond to the above formula where R and $R^3$ are —$CH_3$, $R^1$ is —$C_3H_6$—, $R^2$ is hydrogen, n is zero or 1, m is 1 or 2, a is 7, and b is 0. Also possible is the use of MASIL™ SF19, as obtainable from Lubrizol performance products, Spartanburg, US.

Useful surfactants also include polyether carbosilanes of the formula (7)

(7)

in which Q stands for $R_3$—Si— or $R_3$—Si—(R'—$SiR_2)_a$—R'—$SiR"_2$— where every R in the molecule can be the same or different and stands for an aliphatic $C_1$-$C_{18}$, a cycloaliphatic $C_6$-$C_{12}$ or an aromatic $C_6$-$C_{12}$ hydrocarbon radical, which can optionally be substituted by halogen atoms, R' is a $C_1$-$C_{14}$ alkylene group, R" is R in the case of a≠0 or is R or $R_3SiR'$ in the case of a=0, and a=0-2; P stands for a $C_2$-$C_{18}$ alkylene group, preferably a $C_2$-$C_{14}$ alkylene group or A-R''', where A represents a $C_2$-$C_{18}$ alkylene group and R''' a functional group from the following list: —NHC(O)—, —NHC(O)—$(CH_2)_{n-1}$—, —NHC(O)C(O)—, —NHC(O)$(CH_2)_vC(O)$—, —OC(O)—, —OC(O)—$(CH_2)_{n-1}$—, —OC(O)C(O)—, —OC(O)$(CH_2)_vC(O)$—, —OCH$_2$CH(OH)CH$_2$OC(O)$(CH_2)_{n-1}$—, OCH$_2$CH(OH)CH$_2$OC(O)$(CH_2)_vC(O)$— with v=1-12; T is H or stands for a $C_1$-$C_4$ alkyl radical or a $C_1$-$C_4$ acyl radical; x stands for a number from 1 to 200 and n stands for an average number from 1 to 6, preferably 1 to 4. Thus, the element —$SiR"_2$— can also comprise the substructure —Si(R)($R_3SiR'$)—.

The polyether part can be a homopolymer, but can also be a statistical, alternating or block copolymer.

Suitable polyether carbosilanes are selected from the group consisting of: $Et_3Si$—$(CH_2)_3$—O—$(C_2H_4O)y$-$CH_3$, Et=Ethyl; $Et_3Si$—$CH_2$—$CH_2$—O—$(C_2H_4O)y$-$CH_3$, Et=Ethyl; $(Me_3Si$—$CH_2)_3Si$—$(CH_2)_3$—O—$(C_2H_4O)y$-$CH_3$, Me=Methyl; $Me_3Si$—$CH_2SiMe_2$—$(CH_2)_3$—O—$(C_2H_4O)y$-$CH_3$, Me=Methyl; $(Me_3Si$—$CH_2)_2SiMe$—$(CH_2)_3$—O—$(C_2H_4O)y$-$CH_3$, Me=Methyl; $Me_3Si$—$(CH_2)_3$—O—$(C_2H_4O)y$-$CH_3$, Me=Methyl; $Me_3Si$—$CH_2CH_2$—O—$(C_2H_4O)y$-$CH_3$, Me=Methyl; $Ph_3Si$—$(CH_2)_3$—O—$(C_2H_4O)y$-$CH_3$, Ph=phenyl; $Ph_3Si$—$CH_2$—$CH_2O$—$(C_2H_4O)y$-$CH_3$, Ph=phenyl; $Cy_3Si$—$(CH_2)_3$—O—$(C_2H_4O)y$-$CH_3$, Cy=cyclohexyl; $Cy_3Si$—$CH_2CH_2$—O—$(C_2H_4O)y$-$CH_3$, Cy=cyclohexyl; $(C_6H_{13})_3Si$—$(CH_2)_3$—O—$(C_2H_4O)y$-$CH_3$, $(C_6H_{13})_3Si$—$CH_2CH_2$—O—$(C_4H_4O)$y-$CH_3$ in which y conforms to the relation: 5≤y≤20 and mixtures thereof.

Also preferred is sometimes the use of non-ionic surface-active substances according to the formula (8):

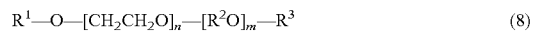

(8)

wherein $R^1$ represents an aromatic or aliphatic, linear or branched hydrocarbon group having at least 8 carbon atoms, $R^2$ represents an alkylene having 3 carbon atoms, $R^3$ represents hydrogen or a C1-C3 alkyl group, n has a value of 0 to 40, m has a value of 0 to 40 and the sum of n+m being at least 2.

It will be understood that in the above formula, the units indexed by n and m may appear as blocks or they may be present in an alternating or random configuration.

Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8. Still further examples include those in which $R^1$ in the above formula represents an alkyl group of 4 to 20 carbon atoms, m is 0 and $R^3$ is hydrogen. An example thereof includes isotridecanol ethoxylated with about 8 ethoxy groups and which is commercially available as GENAPOL™ X080 from Clariant GmbH. Non-ionic surfactants according to the above formula in which the hydrophilic part comprises a block-copolymer of ethoxy groups and propoxy groups may be used as well. Such non-ionic surfactants are commercially available from Clariant GmbH under the trade designation GENAPOL™ PF 40 and GENAPOL™ PF 80. Further suitable non-ionic surfactants that are commercially available include Tergitol™ TMN 6, Tergitol™ TMN 10, or Tergitol™ TMN 100X. Also statistical, alternating or block copolymers of ethylene oxide and propylene oxide are suitable surfactants according to the present invention. Such non-ionic surfactants are available e.g. under the trade name Breox™ A, Synperonic™ or Pluronic™.

A mixture of a silicone moieties containing surfactant and one or more non-ionic surfactants selected from alkoxylated hydrocarbon surfactants can be used, as well.

Surfactants which can also be used, either alone or as a mixture of two or more thereof, can be found in U.S. Pat. No. 5,750,589 (Zech et al), col. 2, l. 47 to col. 3 l. 27 and col. 3, l. 49 to col. 4, l. 4 and col. 5, l. 7 to col. 14, l. 20. Other surfactants which can be used, either alone or as a mixture of two or more thereof, can be found in U.S. Pat. No. 4,657,959 (Bryan et al.), col. 4, l. 46 to col. 6. l. 52 as well as in EP 0 231 420 B1 (Gribi et al.) p 4, l. 1 to p 5, l. 16 and in the examples. Suitable examples are further described e.g. in U.S. Pat. No. 4,782,101 (Waller et al.).

The content of these documents with regards to hydrophilizing agents and their preparation is herewith incorporated by reference.

If present, the surfactant(s) as Component G is present in the following amounts:
Lower limit: at least 0.1 or at least 0.3 or at least 0.5 wt. %;
Upper limit: utmost 15 or utmost 12 or utmost 10 wt. %;
Range: 0.1 to 15 or 0.3 to 12 or 0.5 to 10 wt. %;
wt. % with respect to the weight of the whole composition.

The radiation-curable dental impression composition described in the present text may also comprise in addition to other ingredients and surfactants, alone or in combination an F-containing component as component H including those described in EP 2 442 778 B1 (3M), especially those described on pages 12 to 16, paragraphs [0137] to [0162].

Useful F-containing components may be described by the following formula (9):

$$(G^1\text{-}L^1\text{-}O)_s\text{—}R_f^a\text{—}O\text{-}L^2\text{-}G^2 \quad (9)$$

wherein:
$G^1$ and $G^2$ each independently represents a non-ionic end-group that is free of polyoxyalkylene groups or contains polyoxyalkylene such that the total amount thereof in the F-containing compound is not more than 10 wt. % based on the molecular weight of the F-containing compound;

$L^1$ and $L^2$ each independently represents an aliphatic hydrocarbon group or a partially or fully fluorinated aliphatic hydrocarbon group;
$R_f^a$ represents a mono-valent or divalent partially or fully fluorinated aliphatic group or a partially or fully fluorinated aliphatic group interrupted by one or more oxygen atoms;
with the proviso that at least one of the following conditions is fulfilled:
(i) at least one of the moieties $L^1$-$G^1$ and $L^2$-$G^2$ is partially or fully fluorinated or
(ii) $R_f$ is a partially or fully fluorinated aliphatic group interrupted by one or more oxygen atoms.

More precisely, the F-containing component may be described by the following formula (10):

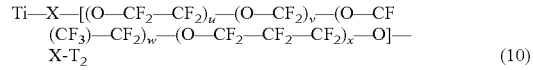
(10)

with u=0 to 8, v=0 to 8, w=0 to 8 and x=0 to 8 and u+v+w+x≥1,
wherein $T_1$ and $T_2$ can be equal or different and are independently selected from —COOR, —CONR$^b$R$^c$—CH$_2$OH, —CF$_2$OR, —CHFOH, —CHFOR, —CH$_2$OR or F with R and being a linear or branched alkyl rest ($C_1$ to $C_9$), aryl rest ($C_1$ to $C_9$) or alkylaryl rest ($C_1$ to $C_9$) each of which may optionally be substituted with one or more substituents selected from the group consisting of hydroxyl, amino group, halogen atom, an SiH group and a group capable of reacting with SiH, $R^b$ and $R^c$ independently representing H or having a meaning as given for R, and wherein X is selected from —(CF$_2$)$_{1-6}$—, —CF(CF$_3$)— and —CHF—CF$_2$—.

Particular examples of the F-containing component include: CF$_3$—O—CF$_2$—O—CF$_2$—CF$_2$—O—CHF-T, CF$_3$—(O—CF$_2$)$_2$—O—CF$_2$—CF$_2$—O—CHF-T, CF$_3$—(O—CF$_2$)$_3$—O—CF$_2$—CF$_2$—O—CHF-T, CF$_3$—O—CF$_2$—O—CF$_2$—CF$_2$—O—CHF—CF$_2$-T, CF$_3$—(O—CF$_2$)$_2$—O—CF$_2$—CF$_2$—O—CHF—CF$_2$-T, CF$_3$—(O—CF$_2$)$_3$—O—CF$_2$—CF$_2$—O—CHF—CF$_2$-T, C$_3$F$_7$—O—CF$_2$—CHF-T, CF$_3$—O—CF$_2$—O—CF$_2$—CF$_2$—O—CF$_2$—CHF-T, CF$_3$—(O—CF$_2$)$_2$—O—CF$_2$—CF$_2$—O—CF$_2$—CHF-T, CF$_3$—(O—CF$_2$)$_3$—O—CF$_2$—CF$_2$—O—CF$_2$—CHF-T, C$_3$F$_7$—O—CF$_2$—CHF—CF$_2$-T, CF$_3$—O—CF$_2$—CF$_2$—O—CF$_2$—CHF—CF$_2$-T, CF$_3$—O—CF$_2$—O—CF$_2$—CF$_2$—O—CF$_2$—CHF—CF$_2$-T, CF$_3$—(O—CF$_2$)$_2$—O—CF$_2$—CF$_2$—O—CF$_2$—CHF—CF$_2$-T, CF$_3$—(O—CF$_2$)$_3$—O—CF$_2$—CF$_2$—O—CF$_2$—CHF—CF$_2$-T, CF$_3$—(O—CF$_2$)$_3$—O—CF$_2$-T, CF$_3$—(O—CF$_2$)$_5$—O—CF$_2$-T, C$_2$F$_5$—(O—CF$_2$—CF$_2$)—O—CF$_2$-T, C$_3$F$_7$—(O—CF$_2$—CF$_2$)$_1$—O—CF$_2$-T, C$_4$F$_9$—(O—CF$_2$—CF$_2$)$_1$—O—CF$_2$-T, C$_2$F$_5$—(O—CF$_2$—CF$_2$)$_2$—O—CF$_2$-T, CF$_3$—(O—CF$_2$—CF$_2$)$_2$—O—CF$_2$-T, C$_3$F$_7$—(O—CF$_2$—CF$_2$)$_2$—O—CF$_2$-T, C$_4$F$_9$—(O—CF$_2$—CF$_2$)$_2$—O—CF$_2$-T, CF$_3$—(CF$_2$)$_2$—(O—CF(CF$_3$)—CF$_2$)$_2$—O—CF(CF$_3$)-T, CF$_3$—(CF$_2$)$_2$—(O—CF(CF$_3$)—CF$_2$)$_3$—O—CF(CF$_3$)-T, CF$_3$—(CF$_2$)$_2$—(O—CF(CF$_3$)—CF$_2$)$_4$—O—CF(CF$_3$)-T, CF$_3$—(CF$_2$)$_2$—(O—CF(CF$_3$)—CF$_2$)$_5$—O—CF(CF$_3$)-T, CF$_3$—(CF$_2$)$_2$—(O—CF(CF$_3$)—CF$_2$)$_6$—O—CF(CF$_3$)-T, CF$_3$—CFH—O—(CF$_2$)$_3$-T, CF$_3$—CFH—O—(CF$_2$)$_5$-T, CF$_3$—CF$_2$—O—(CF$_2$)$_3$-T, CF$_3$—CF$_2$—O—(CF$_2$)$_5$-T, Rf-(O—CF$_2$—CF$_2$—CF$_2$)$_n$—O—CF$_2$—CF$_2$-T, with n=1 to 25 and Rf being a linear or branched per- or partly fluorinated alkyl rest (C1 to C6), wherein the alkyl chain can be interrupted by O atoms, T-CF$_2$—O—(CF$_2$—CF$_2$—O)$_p$—(CF$_2$—O)$_q$—CF$_2$-T, with p/q=0.5 to 3.0 and an molecular weight in the range of 500 to 4,000 g/mol, T-CF$_2$—(O—CF(CF$_3$)—

$CF_2)_n$—(O—$CF_2)_m$—O—$CF_2$-T, with n/m=20 to 40 and a molecular weight in the range of 650 to 3,200 g/mol, and mixtures thereof, wherein T can be equal or different and are independently selected from —COOR, —CONR$^b$R$^c$— $CH_2OH$, —$CF_2OR$, —CHFOH, —CHFOR, —$CH_2OR$ or —F with R and being a linear or branched alkyl rest ($C_1$ to $C_9$), aryl rest ($C_1$ to $C_9$) or alkylaryl rest ($C_1$ to $C_9$) each of which may optionally be substituted with one or more substituents selected from the group consisting of hydroxyl, amino group, halogen atom, an SiH group and a group capable of reacting with SiH, R$^b$ and R$^c$ independently representing H or having a meaning as given for R, and wherein X is selected from —$(CF_2)_{1\text{-}6}$—, —$CF(CF_3)$— and —$CHF$—$CF_2$—.

Suitable fluorinated compounds also include fluorinated polyethers that are commercially available under the tradename FOMBLIN™, GALDEN™ and H-Galden™, Fluorolink™ materials which may be prepared using preparation methods described in US2007/0276068, EP 870877, WO 2004/060964, WO 2007/140091, US 2007/015864, US 2007/015864, US 2007/025902 and US 2007/015937.

HFPO can be obtained as described in U.S. Pat. No. 3,242,218 or US 2004/0124396. The general formula of a methyl ester derivative of HFPO is $C_3F_7O[CF(CF_3)CF_2O]_n$ $CF(CF_3)COOCH_3$ with n being 1 to 8. HFPO-Amidol as described in WO2004/060964 A1 has the formula $CF_3$— $(CF_2)_2$—(O—$CF(CF_3)$—$CF_2)_2$—O—$CF(CF_3)$— $CONHCH_2CH_2OH$.

The use of HFPO and/or HFPO-Amidol in combination with the polyether-modified polydimethyl siloxane described in the present text is sometimes preferred.

If present, the F-containing component H is present in the following amounts:
Lower limit: at least 0.1 or at least 0.3 or at least 0.5 wt. %;
Upper limit: utmost 15 or utmost 12 or utmost 10 wt. %;
Range: 0.1 to 15 or 0.3 to 12 or 0.5 to 10 wt. %;
wt. % with respect to the weight of the whole composition.

The radiation-curable dental impression composition described in the present text can also comprise one or more fluorescent dyes as component (I).

The addition of fluorescent dyes can help to further increase the depth of cure. Fluorescent dyes are able to absorb light and emit the absorbed light also to those regions of the radiation-curable dental impression composition which are not directly accessible by the applied radiation. Thus, fluorescent dyes with an emission maximum at the excitation band of the initiator system is preferred.

According to one embodiment, the fluorescence dye has an absorption maximum between 350 and 470 nm and an emission maximum 400 nm and 500 nm.

According to one embodiment, the dye is characterized by the following features alone or in combination:
a) solubility: at least 0.5 wt. % or at least 0.75 wt. % or at least 1.0 wt. % in PEG 400 at 50° C.;
b) having a light absorption band in the range of 350 to 470 nm;
c) having a fluorescence maximum in the range of 400 to 500 nm;
d) having a fluorescence quantum yield of 20% or more.

A combination of the features a) and b) or a), b) and c) can sometimes be preferred.

Adding a fluorescing dye as described in the present text may help to improve depth of cure of the radiation-curable dental impression composition.

Suitable examples include Coumarin 102 having an absorption maximum at 389 nm and an emission maximum at 465 nm as well as Coumarin 120 having an absorption maximum at 354 nm and an emission maximum at 435 nm and Fluoreszenzviolett 94730 (Kremer) having an absorption maximum at 377 nm and an emission maximum at 433 nm.

The dye(s) is typically present in the following amount(s):
Lower limit: at least 0.001 or at least 0.003 or at least 0.005 wt. %;
Upper limit: utmost 1 or utmost 0.5 or utmost 0.1 wt. %;
Range: 0.001 to 1 or 0.003 to 0.5 or 0.005 to 0.1 wt. %;
wt. % with respect to the weight of the whole composition.

The radiation-curable dental impression composition described in the present text can also comprise one or more additives as component (J).

Suitable additives include pigment(s), astringent(s), flavour(s) and other ingredients well known to those skilled in the art.

Preferred are those ingredients and additives that do not add unpleasant smell or taste.

Compounds that have an unpleasant smell might be removed by thinfilm evaporation, if needed.

If present, additive(s) as Component J are present in the following amounts:
Lower limit: at least 0.05 or at least 0.1 or at least 0.2 wt. %;
Upper limit: utmost 5 or utmost 3 or utmost 2 wt. %;
Range: 0.05 to 5 or 0.1 to 3 or 0.2 to 2 wt. %;
wt. % with respect to the weight of the whole composition.

Examples for pigments include titanium dioxide or zinc sulphide (lithopones), red iron oxide 3395, Bayferrox™ 920 Z Yellow, Neazopon™ Blue 807 (copper phthalocyanine-based dye) or Helio™ Fast Yellow ER.

If present, pigments are typically present in an amount of 0.01 to 3 wt. % with respect to the whole composition.

Astringent(s) which may be included comprise aluminum salts like aluminum sulfate, aluminum ammonium sulfated, aluminum chlorohydrated, aluminum acetate and mixtures thereof. Useful astringent(s) can also contain iron or manganese containing substances.

Incorporating an astringent may help to prevent or reduce the risk of bleeding during use or after removal of the composition from the mouth of a patient.

If present, astringents are typically present in an amount of 0.01 to 3 wt. % with respect to the whole composition.

Flavour(s) which can be used include peppermint oil, menthol, cinnamon oil, spearmint oil, vanilla, wintergreen oil, lemon oil, orange oil, grape, lime oil, grapefruit oil, apple, apricot essence, and mixtures thereof and mixtures thereof.

The addition of additive(s) which have a pleasant smell can be useful.

If additive(s) are present, they are typically present in an amount sufficient and not detrimental to the desired effect or effects to be achieved.

If present, the additive(s) are typically present in the following amounts:
Lower amount: at least 0.05 or 0.1 or 0.5 wt. %;
Upper amount: at most 10 or 8 or 5 wt. %;
Range: 0.05 to 10 or 0.1 to 8 or 0.5 to 5 wt. %;
wt. % with respect to the weight of the whole composition.

According to one embodiment, the radiation-curable dental impression composition comprises:
Component A (mercapto functional polyorganosiloxane): 1 to 20 wt. %;
Component B1 (VQM resin): 10 to 60 wt. %;
Component B2 (organosiloxane): 10 to 70 wt. %;
Component C (photo-initiator): 0.01 to 5 wt. %;

Component D (filler): 0 to 60 wt. %;
Component E (absorber): 0 to 15 wt. %;
Component F (stabilizer): 0 to 1 wt. %;
Component G (surfactant): 0 to 15 wt. %;
Component H (F-containing component): 0 to 15 wt. %;
Component I (fluorescing dye): 0 to 1 wt. %;
Component J (additive): 0 to 10 wt. %;
wt. % with respect to the whole composition.

According to another embodiment, the radiation-curable dental impression composition comprises:
Component A (mercapto functional polyorganosiloxane): 1 to 20 wt. %;
Component B1 (VQM resin): 10 to 60 wt. %;
Component B2 (organosiloxane): 10 to 70 wt. %;
Component C (photo-initiator): 0.01 to 5 wt. %;
Component D (filler): 10 to 60 wt. %;
Component E (absorber): 0 to 15 wt. %;
Component F (stabilizer): 0 to 1 wt. %;
Component G (surfactant): 0.1 to 15 wt. %;
Component H (F-containing component): 0 to 15 wt. %;
Component I (fluorescing dye): 0 to 1 wt. %;
Component J (additive): 0 to 10 wt. %;
wt. % with respect to the whole composition.

According to another embodiment, the radiation-curable dental impression composition comprises:
Component A (mercapto functional polyorganosiloxane): 1 to 20 wt. %;
Component B1 (VQM resin): 10 to 60 wt. %;
Component B2 (organosiloxane): 10 to 70 wt. %;
Component C (photo-initiator): 0.01 to 5 wt. %;
Component D (filler): 10 to 60 wt. %;
Component E (absorber): 0 to 15 wt. %;
Component F (stabilizer): 0 to 1 wt. %;
Component G (surfactant): 0.1 to 15 wt. %;
Component H (F-containing component): 0 to 15 wt. %;
Component I (fluorescing dye): 0.001 to 1 wt. %;
Component J (additive): 0 to 10 wt. %;
wt. % with respect to the whole composition.

According to another embodiment, the radiation-curable dental impression composition comprises:
Component A (mercapto functional polyorganosiloxane): 1 to 20 wt. %;
Component B1 (VQM resin): 10 to 60 wt. %;
Component B2 (organosiloxane): 10 to 70 wt. %;
Component C (photo-initiator): 0.01 to 5 wt. %;
Component D (filler): 10 to 60 wt. %;
Component E (absorber): 1 to 15 wt. %;
Component F (stabilizer): 0 to 1 wt. %;
Component G (surfactant): 0.1 to 15 wt. %;
Component H (F-containing component): 0 to 15 wt. %;
Component I (fluorescing dye): 0 to 1 wt. %;
Component J (additive): 0 to 10 wt. %;
wt. % with respect to the whole composition.

According to another embodiment, the radiation-curable dental impression composition comprises:
Component A (mercapto functional polyorganosiloxane): 1 to 20 wt. %;
Component B1 (VQM resin): 10 to 60 wt. %;
Component B2 (organosiloxane): 10 to 70 wt. %;
Component C (photo-initiator): 0.01 to 5 wt. %;
Component D (filler): 10 to 60 wt. %;
Component E (absorber): 1 to 15 wt. %;
Component F (stabilizer): 0 to 1 wt. %;
Component G (surfactant): 0.1 to 15 wt. %;
Component H (F-containing component): 0 to 15 wt. %;
Component I (fluorescing dye): 0.001 to 1 wt. %;
Component J (additive): 0 to 10 wt. %;
wt. % with respect to the whole composition.

Additional embodiments are described below:

Embodiment 1

A process as described in the present text comprising the step of providing a radiation-curable dental impression composition, wherein
the mercapto-functional polyorganosiloxane(s)
has a fraction of (mercaptoalkyl)methylsiloxane units of 7 to 100 mol %,
and is present in an amount of 0.5 to 50 wt. %,
the VQM resin(s)
has a vinyl content of at least 0.15 mmol/g,
and is present in an amount of 10 to 60 wt. %,
the photo-initiator(s)
has a light absorption band in the range of 350 to 550 nm,
and is present in an amount of 0.01 to 5 wt. %,
the filler(s)
is selected from non-reinforcing fillers, and
is present in an amount of 0 to 60 wt. %,
wt. % with respect to the weight of the whole composition.

Embodiment 2

A process as described in the present text comprising the step of providing a radiation-curable dental impression composition, wherein
the mercapto-functional polyorganosiloxane(s)
has a fraction of (mercaptoalkyl)methylsiloxane units of 7 to 100 mol %,
and is present in an amount of 0.5 to 50 wt. %,
the VQM resin(s)
has a vinyl content of at least 0.15 mmol/g,
and is present in an amount of 10 to 60 wt. %,
the photo-initiator(s)
has a light absorption band in the range of 350 to 550 nm,
and is present in an amount of 0.01 to 5 wt. %,
the filler(s)
is selected from non-reinforcing fillers, and
is present in an amount of 5 to 60 wt. %,
wt. % with respect to the weight of the whole composition.

Embodiment 3

A process as described in the present text comprising the step of providing a radiation-curable dental impression composition, wherein
the mercapto-functional polyorganosiloxane(s)
has a fraction of (mercaptoalkyl)methylsiloxane units of 7 to 100 mol %,
and is present in an amount of 0.5 to 50 wt. %,
the VQM resin(s)
has a vinyl content of at least 0.15 mmol/g,
and is present in an amount of 10 to 60 wt. %,
the photo-initiator(s)
has a light absorption band in the range of 350 to 550 nm,
and is present in an amount of 0.01 to 5 wt. %,
the filler(s)
is selected from non-reinforcing fillers, and
is present in an amount of 0 to 60 wt. %,
the fluorescing dye(s)
is present in an amount of 0.001 to 1 wt. %,
wt. % with respect to the weight of the whole composition.

Embodiment 4

A process as described in the present text comprising the step of providing a radiation-curable dental impression composition, wherein
- the mercapto-functional polyorganosiloxane(s)
  - has a fraction of (mercaptoalkyl)methylsiloxane units of 7 to 100 mol %,
  - and is present in an amount of 0.5 to 50 wt. %,
- the VQM resin(s)
  - has a vinyl content of at least 0.15 mmol/g,
  - and is present in an amount of 10 to 60 wt. %,
- vinylfunctional organosiloxane(s)
  - is present in an amount of 10 to 70 wt. %,
- the photo-initiator(s)
  - has a light absorption band in the range of 350 to 550 nm, and
  - is present in an amount of 0.01 to 5 wt. %,
- the filler(s)
  - is selected from non-reinforcing fillers, and
  - is present in an amount of 0 to 60 wt. %,
- fluorescing dye(s)
  - is present in an amount of 0.001 to 1 wt. %, wt. % with respect to the weight of the whole composition.

The radiation-curable dental impression composition described in the present text does typically not comprise the following component(s) alone or in combination:
- Pt-catalyst, in an amount of more than 0.00001 wt. % calculated with respect to the weight of Pt;
- components comprising (meth)acrylate moieties in an amount of more than 5 wt. % or more than 2 wt. % or more than 1 wt. %;
- components comprising epoxy moieties in an amount of more than 5 wt. % or more than 2 wt. % or more than 1 wt. %;

wt. % with respect to the whole composition.

Thus, the radiation-curable composition is essentially free of any of these components.

The radiation-curable dental impression composition described in the present text can be produced by mixing the respective components, e.g. by using a speed mixer, dissolver or a kneading machine.

The mixing is typically done under safe-light conditions.

During storage, the radiation-curable dental impression composition described in the present text is typically packaged in a suitable packaging device.

The radiation-curable dental impression composition described in the present text is typically stored in container. Suitable containers include vessels, foil bags, cartridges, etc.

The volume of the respective containers is not particularly limited, but is typically in a range of 2 to 200,000 ml or 5 to 100,000 ml or 10 to 50,000 ml.

The radiation-curable dental impression composition described in the present text is typically provided under safe-light conditions before a use. This is beneficial for improving the storage stability and/or shelf life.

The storage of the radiation-curable dental impression composition can also be done together with a dental impression tray.

Thus, the invention also relates to a dental impression tray containing the radiation-curable dental impression composition described in the present text.

The dental impression tray is typically a single-use tray. Further, the dental impression tray is typically transparent for the radiation to be used for curing the radiation-curable dental impression composition.

The invention is directed to a process of taking a dental impression, the process comprises the steps of
- providing the radiation-curable dental impression composition described in the present text,
- applying the radiation-curable dental impression composition to a surface, in particular to the surface of dental tissue,
- applying radiation suitable for initiating the curing of the radiation-curable dental impression composition,
- letting the radiation-curable dental impression composition cure,
- removing the cured dental impression composition from the surface.

The surface can be the surface of soft or hard dental tissue, preferably the surface of a tooth or tooth stump.

Thus, the radiation-curable dental impression composition can be used e.g. for making impressions of soft and hard dental tissue. This can be achieved simply, e.g. filling the material into a dental impression tray and putting the tray into the mouth of a patient.

The curing is initiated by applying radiation is typically carried out at a temperature below 50° C. and preferably below 40° C.

The material is generally regarded as cured, if the cured material fulfils the requirements for its use. For example, a dental precision impression material typically fulfils the requirements for its use when it fulfils the requirements of ISO 4823:2015-08 (such as compatibility with gypsum, strain in compression, recovery from deformation, detail reproduction, linear dimensional change).

The radiation-curable dental impression composition can also be used for the production of crowns and/or bridges, including temporary or long-term crowns and bridges.

In the latter case, after curing the dental impression composition is used as a mould to be filled with the (temporary or long term) crown and/or bridge material, which is typically based on polymerizable (meth)acrylates or similar chemical reactants.

The radiation-curable dental impression composition is especially useful as or for producing precision impression materials, bite registration materials, duplicating materials, modelling materials, situation impression materials.

The cured dental impression composition can typically be characterized by one or more of the following features:
- a) Shore hardness A: 30 to 90, if determined according to DIN ISO 7619-1;
- b) tensile strength: at least 1.0 MPa according to DIN 53504:2015-08;
- c) elongation at break: at least 80%, if determined according to DIN 53504:2015-08, 24 h;
- d) being rubber elastic,
- e) having a water-contact angle: equal to or smaller than 90°.

A combination of the features a) and b); a) and c); b) and e) or a), b) and e) can sometimes be preferred.

The invention is also directed to a kit of parts comprising the radiation-curable dental impression composition described in the present text and the following items alone or in combination: dental impression tray, application syringe, light-curing device, dental retraction material, crown and bridge material.

Dental impression trays and/or application syringes are typically used for applying the composition described in the present text during a dental impressioning process.

Examples of dental impression trays are described e.g. in U.S. Pat. No. 1,509,376 (Rogers) or U.S. Pat. No. 5,487,662 (Kipke et al). The content of these documents is herewith incorporated by reference.

Light-curing devices are known in the art and are typically used for curing composite dental filling materials and dental adhesives.

Examples of light-curing devices are described e.g. in US 2015/202032 A1 (Benz) or U.S. Pat. No. 6,159,005 (Herold et al.). The content of these documents is herewith incorporated by reference.

Dental retraction materials are often used for widening the sulcus of a tooth or teeth shortly before the dental impression is taken.

Examples of dental retraction materials are described e.g. in US 2012/077142 A1 (Maurer et al.) or US 2007/065770 A1 (Lampl et al.) or WO 2018/085744 A1 (3M). The content of these documents is herewith incorporated by reference.

Crown and bridge materials are typically used after a dental impression process has been completed for producing a crown or bridge for the prepared tooth which should be restored.

Examples of crown and bridge materials are described e.g. in U.S. Pat. No. 8,329,776 B2 (Hecht et al.) or U.S. Pat. No. 9,782,329 B2 (Hecht et al.). The content of these documents is herewith incorporated by reference.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof. The following examples are given to illustrate the invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Viscosity

If desired, the viscosity can be measured at 23° C. using a ThermoHaake Rotovisco 1 device with a plate/plate system (diameter 20 mm) and a slit of 0.1 mm. The viscosity values (Pa*s) and share stress values (Pa) can be recorded for each share rate (starting from 10 l/s to 100 l/s in 10 l/s steps. For each share rate, a delay of 5 seconds was used before collecting data. The above-mentioned method of measurement corresponds essentially to DIN 53018-1.

Consistency

If desired, the consistency can be determined according to ISO 4823:2017 with the provision that no mixing of pastes needs to take place (1 component only). The pressed specimen are cured for 20 sec. from one side with a 3M Elipar™ at 395 nm wavelength (1000 W/cm²)

Tensile Strength and Elongation at Break

The tensile strength and elongation of the compositions was determined according to DIN 53504:2017-03. The tensile strength is given in MPa and the elongation in % of the original length. Tensile strength and elongation data were evaluated by tearing three I-shaped specimens with a central unit of 20 mm×4 mm×2 mm in a Zwick Z020 Universal testing machine. The pastes were filled into a brass mould and each section is light-cured on both sides at 23° C. for overall 40 sec. using a curing light with 395 nm LED and a power of 630 mW/cm². After removal from the molds, the specimens were post-cured in an Otoflash™ device under argon atmosphere for 1,000 flashes. At least five measurements were conducted and the mean value determined (speed 200 mm/min). The specimens were stored for a waiting time 1-24 h at ambient conditions after post-curing until the measurement is conducted.

Shore A Hardness

If desired, the Shore A hardness of the compositions can be determined according to DIN 53505:2000-08 and measured 10 min after start of light curing. All samples are light-cured for 20 sec from both sides using a curing light containing 395 nm LED with a power of 1000 mW/cm².

Depth of Cure

The depth of cure was determined in accordance with DIN EN ISO 6874:2015. The test is performed in a cylindrical metal form having a diameter of 4 mm and a length of 8 mm.

Because of the elasticity of the resulting specimens instead of a measurement screw a ruler was used to measure the length of the specimen. The curing was done for 10 sec using a 3M Elipar™ S10 with a LED emitting at 395 nm and 1000 mW/cm².

Water Contact Angle Measurement of Cured Composition

If desired, the water contact angle can be determined as follows: For the preparation of test sample the mixed paste is subjected to an object slide and flattened to obtain a homogenous 200 μm thick layer. The object slide is placed on the table of a Drop Shape Analyse System DSA 30 (Kruss GmbH, Hamburg). At the time of 15 to 20 minutes after start of mixing 5 μl of water are placed onto the surface of the specimen and a video (25 frames per second) recording is started to observe the droplet on the surface. The water contact angle is then calculated from the recorded video evaluating the first measurable contact angle of the droplet on the surface. The data (video sequences) is evaluated by the "circle fitting" method, another standard method for data evaluation (see G. Kugel, T. Klettke, J. A. Goldberg, J. Benchimol, R. D. Perry, S. Sharma, J. Prosthod. 2007, 16, 84-92).

Materials

TABLE 1

| | |
|---|---|
| Poly(mercaptopropyl)methylsiloxane 75-100 cSt (75-100 mPa*s); homopolymer | Mercapto-functional polyorganosiloxane |
| VQM-Resin 1: 0.18 mmol/g vinyl; 10,000 mPa*s; Evonik VQM 903; 20 wt. % VQM resin content | VQM resin |
| VQM-Resin 2: 0.72 mmol/g vinyl; 800 mPa*s; Evonik VQM 881; 39 wt. % VQM resin content | VQM resin |
| VQM-Resin 3: 0.34 mmol/g vinyl; 30,000 mPa*s; Evonik VQM 973; 45 wt. % VQM resin content | VQM resin |
| VQM-Resin 4: 0.23 mmol/g vinyl; 1000 mPa*s; Evonik VQM 909; 20 wt. % VQM resin content | VQM resin |

TABLE 1-continued

| | |
|---|---|
| Polymer VS 10000; 10,000 mPa*s, Evonik | Linear vinyl terminated polydimethylsiloxane |
| Polymer VS 1000; 1,000 mPa*s, Evonik | Linear vinyl terminated polydimethylsiloxane |
| Polymer VS 2000; 2,000 mPas, Evonik | Linear vinyl terminated polydimethylsiloxane |
| Aerosil ™ R202 | Filler |
| Cristobalit | Filler |
| Zeoflair ™ 800, | Zeolith, Absorber |
| Omnirad ™ 2022, IGM Resins | Photo-initiator |
| Irganox ™ 1010 | Stabilizer |
| Hostanox ™ P-EPQ | Stabilizer |
| Silwet ™ L-77 | Surfactant |

Preparation

All compositions described in Table 1 were prepared by homogenizing the respective components to a uniform paste using a planetary mixer with vacuum capabilities (Speedmixer DAC 600.1 VAZ-P).

Formulations

All Formulations are given in parts by weight.

TABLE 2

| Component in weight-% | EX1 | EX2 | CEX3 | CEX4 |
|---|---|---|---|---|
| Poly (mercaptopropyl)methyl siloxane 75-100 cSt | 4.0 | 4.2 | 4.0 | 4.0 |
| VQM Resin 1 | 62.5 | | | |
| VQM Resin 2 | 8.2 | | | |
| VQM Resin 3 | | 52.3 | | |
| VQM Resin 4 | | 18.0 | | |
| Polymer VS 10000 | | | 62.5 | |
| Polymer VS 1000 | | | 8.2 | |
| Polymer VS 2000 | | | | 45 |
| Aerosil R202 | 3.4 | 3.4 | 3.4 | 3.4 |
| Cristobalit | 20.0 | 15.00 | 20.0 | 45.7 |
| Zeoflair 800 | | 5.00 | | |
| Omnirad 2022 | 0.3 | 0.3 | 0.3 | 0.3 |
| Irganox 1010 | 0.1 | 0.1 | 0.1 | 0.1 |
| 0.4 wt. % Hostanox P-EPQ + 0.4 wt. % Irganox 1010 in Silwet L-77 | 1.5 | 1.5 | 1.5 | 1.5 |

Results:

TABLE 3

| | EX1 | EX2 | CEX3 | CEX 4 |
|---|---|---|---|---|
| Tensile strength [MPa] | 2.29 | 3.83 | 0.42 | 0.77 |
| Elongation at break [%] | 252 | 207 | 1,479 | 1,700 |
| Viscosity at 50 s⁻¹ [Pa*s] | 29.1 | 67.2 | 18.9 | 29.2 |
| Depth of Cure [mm] | 5 | 5 | 5 | 3 |
| Total amount of filler [%] | 23.4 | 23.4 | 23.4 | 49.1 |
| Total amount of VQM Resin [%] | 15.7 | 27.7 | 0.0 | 0.0 |

Formulations using QM Resins (EX1 and EX2) made it possible to reach high tensile strength values combined with a low filler content, which increases the depth of cure to 5 mm.

Formulations with linear vinyl-terminated Polydimethylsiloxanes (CEX3 and CEX4) showed a lower tensile strength and a lower or equal viscosity, which increases with higher filler loading. At the same time this higher filler loading caused a lower depth of cure.

Using VQM resins in combination with mercapto-functional polyorganosiloxane(s) provide a unique opportunity for radiation-curable materials to increase tensile strength of the cured composition and depth of cure at the same time.

What is claimed is:

1. A process of taking a dental impression, the process comprising the steps of
   providing a radiation-curable dental impression composition,
   placing the radiation-curable dental impression composition in contact with dental tissue,
   applying radiation to the radiation-curable dental impression composition,
   letting the radiation-curable dental impression composition cure,
   removing the cured dental impression composition from the dental tissue,
   the radiation-curable dental impression composition comprising
   mercapto-functional polyorganosiloxane(s) as Component A,
   VQM resin(s) as Component B1,
   photo-initiator(s) as Component C for initiating a curing reaction between Component A and Component B1,
   optionally filler(s) as Component D
   the mercapto-functional polyorganosiloxane according to Component A comprising the following features:
   fraction of (mercaptoalkyl)methylsiloxane units: 7-100 mol-%;

formula: $[(CH_3)_2RSiO_{1/2}]_w[(CH_3)_3SiO_{1/2}]_x[(CH_3)_2SiO]_y[R(CH_3)SiO]_z$, with w being 0 to 0.1, x being 0 to 0.1 and w+x being 0.01 to 0.1, y being 0 to 0.93, z being 0.07 to 0.99, wherein each R is independently selected from a mercapto $C_{1-10}$ hydrocarbyl group; and
   molecular weight (Mn): 500 to 20,000 g/mol;
   the VQM resin comprising the following features:
   concentration of unsaturated moieties: at least 0.15 mmol/g;
   viscosity: 500 to 90,000 mPa*s at 23° C.

2. The process according to claim 1, the radiation having a wave length in the range of 350 to 550 nm.

3. The process according to claim 1, the mercapto-functional polyorganosiloxane according to Component A comprising the following features alone or in combination:
   viscosity: 10 to 1,000 mPa*s at 23° C.;
   amount: 0.5 to 50 wt. % with respect to the weight of the whole composition.

4. The process according to claim 1, the VQM resin being present in an
   amount of 10 to 60 wt. % with respect to the weight of the whole composition.

5. The process according to claim 1 comprising in addition vinylfunctional organosiloxane(s) as Component B2, having the following structure:

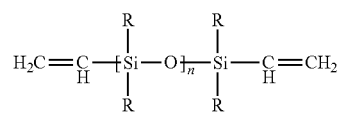

wherein R independently represent a non-substituted or substituted, monovalent hydrocarbon group with 1 to 6 C atoms and wherein n is in the range of 3 to 10,000.

6. The process according to claim 1, the filler(s) comprising following features alone or in combination:
   selected from one or more non-reinforcing fillers;
   having a BET surface of 0.05 to 50 m²/g.

7. The process according to claim 1, the radiation-curable dental impression composition, wherein
   the mercapto-functional polyorganosiloxane(s)
      has a fraction of (mercaptoalkyl) methylsiloxane units of 7 to 100 mol-%,
      and is present in an amount of 0.5 to 50 wt. %,
   the VQM resin(s)
      has a vinyl content of at least 0.15 mmol/g,
      and is present in an amount of 10 to 60 wt. %,
   the photo-initiator(s)
      has a light absorption band in the range of 350 to 550 nm,
      and is present in an amount of 0.01 to 5 wt. %,
   the filler(s)
      is selected from non-reinforcing fillers,
      and is present in an amount of 0 to 60 wt. %,
   wt. % with respect to the weight of the whole composition.

8. The process according to claim 1 comprising in addition absorber(s) selected from zeolite(s), molecular sieve(s) and cyclodextrine(s) as Component E, in an amount of 0.1 to 5 wt. %, wt. % with respect to the whole composition.

9. The process according to claim 1 comprising in addition stabilizer(s) as Component F, in an amount of 0.001 to 1 wt. %, wt. % with respect to the whole composition.

10. The process according to claim 1, comprising in addition the following components alone or in combination:
   surfactant(s) as Component G, in an amount of 0.1 to 15 wt. %;
   F-containing component as Component H, in an amount of 0.1 to 15 wt. %;
   wt. % with respect to the whole composition.

11. The process according to claim 1 comprising in addition fluorescing dye(s) as Component I, in an amount of 0.001 to 1 wt. %, wt. % with respect to the whole composition.

12. The process according to claim 1, the radiation-curable dental impression composition comprising the following features alone or in combination:
   being a paste;
   having a consistency of 27-47 mm according to ISO 4823:2017;
   having a viscosity of 5 to 80 Pa*s at 23° C.;
   having a depth of cure of 2 to 8 mm according to DIN EN ISO 6874:2015.

* * * * *